(12) United States Patent
Yamazaki et al.

(10) Patent No.: US 6,210,698 B1
(45) Date of Patent: Apr. 3, 2001

(54) SUPPOSITORY COMPOSITION

(75) Inventors: Masaru Yamazaki, Hyogo; Soichi Itoh, Osaka; Seiichi Hori, Saitama; Tomoko Fujimori, Saitama; Katsuyoshi Aikawa, Saitama, all of (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/529,022

(22) PCT Filed: Oct. 7, 1998

(86) PCT No.: PCT/JP98/04522

§ 371 Date: Apr. 6, 2000

§ 102(e) Date: Apr. 6, 2000

(87) PCT Pub. No.: WO99/17737

PCT Pub. Date: Apr. 15, 1999

(30) Foreign Application Priority Data

Oct. 8, 1997 (JP) .................................................. 9-275432
Jan. 9, 1998 (JP) ................................................ 10-003422

(51) Int. Cl.⁷ ..................................................... A61K 9/02
(52) U.S. Cl. .......................... 424/434; 424/405; 424/484; 424/486; 424/436; 424/430; 424/433; 514/772.6
(58) Field of Search .................................... 424/436, 434, 424/405, 484, 486; 514/772.6, 965, 966, 946, 947

(56) References Cited

U.S. PATENT DOCUMENTS 5,434,182 * 7/1995 Isaacs et al. ........................ 514/546

FOREIGN PATENT DOCUMENTS

| 54-160713 | 12/1979 | (JP) | ................................. | A61K/9/48 |
| 2-076816 | 3/1990 | (JP) | ................................. | A61K/31/54 |
| 4-346916 | 12/1992 | (JP) | ................................. | A61K/9/02 |
| 5-178763 | 7/1993 | (JP) | ................................. | A61K/47/14 |

* cited by examiner

Primary Examiner—Thurman K. Page
Assistant Examiner—Rachel M. Bennett
(74) Attorney, Agent, or Firm—Sughrue, Mion, Zinn, Macpeak & Seas, PLLC

(57) ABSTRACT

Compositions for suppositories comprising (A) a fatty base, (B) monodecanoyl-glycerol, (C) monolauroyl-glycerol, (D) a powder insoluble in fatty base and (E) a drug for suppositories capable of giving highly useful suppositories which sustain a melting point higher than the body temperature under dry storage conditions and thus remain stable without melting during storage but, when inserted into body cavity, quickly melt or gel.

6 Claims, No Drawings

SUPPOSITORY COMPOSITION

This application is a 371 of PCT/JP98/04522 filed on Oct. 7, 1998.

TECHNICAL FIELD

This invention relates to a composition for suppositories. More particularly, it relates to a composition for suppositories which comprises (A) a fatty base, (B) monodecanoyl-glycerol, (C) monolauroyl-glycerol, (D) a powder insoluble in fatty base and (E) a drug for suppositories.

BACKGROUND ART

Suppository bases are classified into fatty bases and water-soluble bases. Although they are both excellent bases, the fatty bases have been widely employed, since they are superior to the water-soluble ones in less irritation to the administration sites, etc. It has been a practice to design suppositories containing fatty bases to melt at the body temperature. When inserted into a body cavity, therefore, such a suppository would migrate upward from the administration site.

In the case of antihemorrhoidal suppository, drugs should be retained around the affected part. Accordingly, there have been reported a number of compositions for suppositories for preventing drugs from spreading over the rectum by, for example, JP-A-54-26325, JP-A-6-40889, JP-A-63-280016, JP-A-1-143825, JP-A-61-109710, JP-A-2-15024, JP-A-4-164023 and EP No. 103995 (the term "JP-A" as used herein means an "unexamined published Japanese patent application").

However, there has been reported no suppository which sustains a melting point higher than the body temperature and thus never melts during storage but, when inserted into a body cavity, melts or gels at the body temperature owing to a decrease in its melting point.

DISCLOSURE OF THE INVENTION

Suppositories comprising fatty bases would melt at the body temperature after inserted into body cavity such as rectum or vagina and then release drugs contained therein, thus exerting the efficacy. That is to say, suppositories containing fatty bases are designed so that they melt at the human body temperature. Accordingly, it is frequently observed that such suppositories melt during transportation or storage at high temperatures in summer. After melting, suppositories are deformed or dented and thus become unusable. Moreover, the drug distribution becomes less uniform due to the sedimentation of the drug. It is therefore necessary to transport and store suppositories at low temperatures.

An object of the present invention is to provide compositions for suppositories which sustain a melting point higher than the body temperature under dry storage conditions and thus remain stable without melting during transportation or storage but, when inserted into body cavity, quickly melt or gel at the body temperature. Another object of the present invention is to provide compositions for suppositories aiming at treating affected parts in body cavity such as hemorrhoids which are retained at the affected part without spreading out therefrom.

The present inventors conducted extensive studies on compositions for suppositories. As a result, they have successfully obtained compositions for suppositories which sustain a melting point higher than the body temperature under dry storage conditions but, when inserted into body cavity, become moist due to the moisture in the cavities and thus quickly melt or gel at the body temperature. The present invention has been completed based on this finding.

Accordingly, the present invention provides a composition for suppositories which comprises (A) a fatty base, (B) monodecanoyl-glycerol, (C) monolauroyl-glycerol, (D) a powder insoluble in fatty base and (E) a drug for suppositories.

The present invention further provides a composition for suppositories which aims at treating affected parts in body cavity such as hemorrhoids and is prepared by adding a retentive base for intracavity administration to the above-mentioned composition for suppositories.

By adding a vasoconstrictor as the drug for suppositories, furthermore, the obtained composition for suppositories can prevent the drug from spreading out from the affected tissue and elevate the drug concentration in the tissue, thus achieving a potentiated efficacy.

The fatty bases to be used in the present invention are fatty acid triglycerides exemplified by cacao fat, lanolin fat, medium-chain fatty acid triglycerides and hard fats. Examples of the hard fats include Witepsol (manufactured by Huls Aktiengesellschaft), Saposyer (manufactured by Gattefoss), Isocacao (manufactured by Kao) and Pharmasol (manufactured by Nippon Oils and Fats).

The term "powder insoluble in fatty base" means a powder which is insoluble in fatty acid triglycerides. Examples thereof include anhydrous silicic acid, starches, crystalline cellulose, zinc oxide and alginic acid. It is preferable to use anhydrous silicic acid therefor.

The term "drug for suppositories" means a drug which is usually administered in the dosage form of suppositories. Examples thereof include anti-inflammatory, antipyretic and analgesic agents such as acetylsalicylic acid, acetaminophen, buprenorphine hydrochloride, indomethacin, ibuprofen, ketoprofen, piroxicam, diclofenac sodium, morphine hydrochloride, lysozyme hydrochloride and glycyrrhetinic acid; antibiotics such as penicillin, cephalosporin, tetracycline and macrolides; antitumor agents such as 5-fluorouracil and futraful; antifungal agents such as econazole, econazole nitrate, miconazole, miconazole nitrate, clotrimazole, bifonazole, terbinafine hydrochloride and butenafine hydrochloride; steroids such as hydrocortisone, hydrocortisone acetate, prednisolone, dexamethasone and dexamethasone acetate; local anesthetics such as ethyl aminobenzoate, lidocaine, lidocaine hydrochloride, dibucaine, dibucaine hydrochloride, procaine, procaine hydrochloride, meprylcaine, meprylcaine hydrochloride and mepivacaine; astringents such as zinc oxide, tannic acid, albumin tannate and aluminum potassium sulfate; antihistaminic agents such as diphenhydramine, diphenhydramine hydrochloride and chlorpheniramine maleate; wound healing promoters such as allantoin and aluminum chlorhydroxy allantoin; bactericides such as chlorhexidine hydrochloride, cetrimide, decalinium chloride or benzalkonium chloride; sulfa drugs such as sulfisomidine, sulfisomidine sodium, homosulfamine or sulfadiazine; vitamins such as liver oil, ergocalciferol, riboflavin, pyridoxine hydrochloride and tocopherol acetate; refrigerants such as d-camphor, dl-camphor, l-menthol, dl-menthol, peppermint oil and eucalyptus oil; antiemetic agents such as domperidone; defecation promoters such as bisacodyl; bronchodilating agents such as theophylline; peptides such as insulin; and vasoconstrictors such as tetrahydrozoline hydrochloride, naphazoline hydrochloride, phenylephrine hydrochloride, ephedrine hydrochloride and oximetazoline hydrochloride.

When vasoconstrictors such as tetrahydrozoline hydrochloride, naphazoline hydrochloride, phenylephrine hydrochloride, ephedrine hydrochloride and oxymetazoline hydrochloride are added to compositions for suppositories containing retentive bases for intracavity administration, the retention of the drugs can be enhanced in the affected sites located in the lower parts of body cavity.

The term "retentive base for intracavity administration" means a base ingredient allowing the retention of drugs around affected sites in the lower parts of body cavity. Examples thereof include acrylic acid polymers, Polygam alkali metal salts, layered silicate minerals, starch acrylate, polyvinyl alcohol, pectin, cellulose derivatives (methylcellulose, carboxymethylcellulose, etc.), polyvinyl pyrrolidone, pullulan and tragacanth gum. It is preferable to use acrylic acid polymers therefor. Among all, carboxyvinyl polymer may be cited as the most desirable one.

Based on the total weight of the composition for suppositories, the content of a fatty base (A) is from 25 to 85% by weight, preferably from 40 to 70% by weight; the content of monodecanoyl-glycerol (B) is from 0.1 to 30% by weight, preferably form 3 to 10% by weight; the content of monolauroyl-glycerol (C) is from 10 to 70% by weight, preferably from 15 to 50% by weight; the content of a powder insoluble in fatty base (D) is from 0.1 to 20% by weight, the content of anhydrous silicic acid, if employed, is from 0.5 to 10%; and the content of a drug for suppositories (E) is from 0.1 to 20% by weight.

When a retentive base for intracavity administration is further added, the content of a fatty base (A) is from 30 to 85% by weight, preferably from 40 to 70% by weight; the content of monodecanoyl-glycerol (B) is from 0.1 to 30% by weight, preferably from 1 to 10% by weight; the content of monolauroyl-glycerol (C) is from 5 to 65% by weight, preferably from 10 to 45% by weight; the content of a powder insoluble in fatty base (D) is from 0.1 to 20% by weight, the content of anhydrous silicic acid, if employed, is from 0.5 to 10%; the content of a drug for suppositories (E) is from 0.1 to 20% by weight and the content of a retentive base for intracavity administration (F) is from 0.1 to 20% by weight, each based on the total weight of the composition for suppositories.

The content of carboxyvinyl polymer, which is the most desirable example of the retentive base for intracavity administration, is from 0.2 to 15% by weight, still preferably from 1 to 10% by weight, based on the total weight of the composition for suppositories.

The content of a vasoconstrictor is from 0.005 to 2.0% by weight based on the total weight of the composition for suppositories. More particularly speaking, it is preferable to use from 0.005 to 0.1% by weight of tetrahydrozoline hydrochloride, naphazoline hydrochloride or oximetazoline hydrochloride.

During storage, the composition for suppositories of the present invention has a melting point preferably falling within a range of from about 40 to 50° C. When inserted into a body cavity, it preferably has a melting point of from about 36 to 37° C.

By using the composition for suppositories of the present invention, suppositories may be produced in the following manner. First, a fatty base, monodecanoyl-glycerol and monolauroyl-glycerol are mixed together in a melted state optionally with a retentive base for intracavity administration. Next, a drug and a powder insoluble in fatty base are added thereto and uniformly mixed by stirring. Then the resultant mixture is filled in containers, molds, etc. where it is then solidified by cooling. The mixing may be performed by an arbitrary method without restriction.

The suppositories produced by using the compositions for suppositories of the present invention can be administered intrarectally, intravaginally or urethrally.

INDUSTRIAL APPLICABILITY

The suppositories produced by using the compositions for suppositories of the present invention have a melting point higher than the body temperature under the dry storage conditions and thus remain stable without melting upon changes in temperature during transportation or storage. When inserted into body cavity, the suppositories become moist due to the moisture in the cavities and thus the melting point thereof is lowered. As a result, the suppositories melt or gel at the body temperature. Namely, the suppositories with the use of the compositions for suppositories of the present invention are highly useful ones which can be easily handled during transportation and storage and ensure good melting and efficacious drug-release in body cavity.

To further illustrate the present invention in greater detail, the following Examples will be given.

EXAMPLE 1

| (Formulation) | |
|---|---|
| ketoprofen | 50 mg |
| monodecanoyl-glycerol | 75 mg |
| monolauroyl-glycerol | 225 mg |
| light anhydrous silicic acid | 10 mg |
| Pharmasol B115 | 450 mg. |

(Production method)

To the fatty base (Phamasol B115) melted by heating (50–80° C.) were successively added other ingredients under stirring and dispersed therein. After cooling to about 50° C., the mixture was filled into suppository containers and molded by further cooling to give suppositories.

EXAMPLE 2

| (Formulation) | |
|---|---|
| ketoprofen | 50 mg |
| monodecanoyl-glycerol | 37.5 mg |
| monolauroyl-glycerol | 225 mg |
| light anhydrous silicic acid | 10 mg |
| Pharmasol B115 | 487.5 mg. |

(Production method)

The procedure of Example 1 was repeated.

EXAMPLE 3

| (Formulation) | |
|---|---|
| lidocaine | 60 mg |
| hydrocortisone acetate | 5 mg |
| allantoin | 20 mg |
| tocopherol acetate | 50 mg |
| monodecanoyl-glycerol | 80 mg |
| monolauroyl-glycerol | 560 mg |

-continued

| (Formulation) | |
|---|---|
| light anhydrous silicic acid | 20 mg |
| Pharmasol B115 | 905 mg. |

(Production Method)
The procedure of Example 1 was repeated.

EXAMPLE 4

| (Formulation) | |
|---|---|
| acetaminophen | 100 mg |
| monodecanoyl-glycerol | 35 mg |
| monolauroyl-glycerol | 140 mg |
| light anhydrous silicic acid | 10 mg |
| Witepsol H15 | 525 mg. |

(Production Method)
The procedure of Example 1 was repeated.

EXAMPLE 5

| (Formulation) | |
|---|---|
| acetaminophen | 100 mg |
| monodecanoyl-glycerol | 35 mg |
| monolauroyl-glycerol | 140 mg |
| light anhydrous silicic acid | 10 mg |
| macrogol 4000 | 35 mg |
| Witepsol H15 | 490 mg. |

(Production Method)
The procedure of Example 1 was repeated.

EXAMPLE 6

| (Formulation) | |
|---|---|
| diclofenac sodium | 25 mg |
| monodecanoyl-glycerol | 35 mg |
| monolauroyl-glycerol | 220 mg |
| light anhydrous silicic acid | 10 mg |
| macrogol 4000 | 35 mg |
| Witepsol H15 | 475 mg. |

(Production Method)
The procedure of Example 1 was repeated.

EXAMPLE 7

| (Formulation) | |
|---|---|
| miconazole nitrate | 100 mg |
| monodecanoyl-glycerol | 45 mg |
| monolauroyl-glycerol | 225 mg |
| light anhydrous silicic acid | 10 mg |
| macrogol 4000 | 45 mg |
| Witepsol H15 | 575 mg. |

(Production Method)
The procedure of Example 1 was repeated.

EXAMPLE 8

| (Formulation) | |
|---|---|
| tetrahydrozoline hydrochloride | 1 mg |
| lidocaine | 60 mg |
| hydrocortisone acetate | 5 mg |
| allantoin | 20 mg |
| tocopherol acetate | 60 mg |
| light anhydrous silicic acid | 20 mg |
| monodecanoyl-glycerol | 80 mg |
| monolauroyl-glycerol | 560 mg |
| Pharmasol B115 | 960 mg. |

(Production Method)
The procedure of Example 1 was repeated.

EXAMPLE 9

| (Formulation) | |
|---|---|
| phenylephrine hydrochloride | 1.3 mg |
| dibucaine | 1.8 mg |
| hydrocortisone acetate | 1.3 mg |
| zinc oxide | 40 mg |
| light anhydrous silicic acid | 20 mg |
| carboxyvinyl polymer | 20 mg |
| monodecanoyl-glycerol | 165 mg |
| monolauroyl-glycerol | 500 mg |
| Pharmasol B115 | 905 mg. |

(Production Method)
The procedure of Example 1 was repeated.

EXAMPLE 10

| (Formulation) | |
|---|---|
| naphazoline hydrochloride | 1 mg |
| lidocaine | 60 mg |
| prednisolone acetate | 1 mg |
| allantoin | 20 mg |
| tocopherol acetate | 60 mg |
| light anhydrous silicic acid | 20 mg |
| carboxyvinyl polymer | 20 mg |
| monodecanoyl-glycerol | 80 mg |
| monolauroyl-glycerol | 420 mg |
| Witepsol H15 | 930 mg. |

(Production Method)
The procedure of Example 1 was repeated.

EXAMPLE 11

| (Formulation) | |
|---|---|
| naphazoline hydrochloride | 1 mg |
| lidocaine | 60 mg |
| hydrocortisone acetate | 5 mg |
| diphenhydramine hydrochloride | 10 mg |
| allantoin | 20 mg |
| tocopherol acetate | 50 mg |
| zinc oxide | 100 mg |

-continued (Formulation)

| | |
|---|---|
| Laponite | 70 mg |
| monodecanoyl-glycerol | 70 mg |
| monolauroyl-glycerol | 260 mg |
| Witepsol H15 | 1000 mg. |

(Production Method)
The procedure of Example 1 was repeated.

EXAMPLE 12

(Formulation)

| | |
|---|---|
| tetrahydrozoline hydrochloride | 1 mg |
| lidocaine | 60 mg |
| prednisolone acetate | 1 mg |
| crotamiton | 50 mg |
| chlorhexidine hydrochloride | 5 mg |
| aluminum chlorohydroxy allantoinate | 5 mg |
| tocopherol acetate | 50 mg |
| starch acrylate | 65 mg |
| monodecanoyl-glycerol | 150 mg |
| monolauroyl-glycerol | 450 mg |
| Witepsol W35 | 820 mg. |

(Production Method)
The procedure of Example 1 was repeated.

Comparative Example 1

(Formulation)

| | |
|---|---|
| ketoprofen | 50 mg |
| light anhydrous silicic acid | 10 mg |
| Pharmasol B115 | 750 mg. |

(Production Method)
The procedure of Example 1 was repeated.

Comparative Example 2

(Formulation)

| | |
|---|---|
| ketoprofen | 50 mg |
| monolauroyl-glycerol | 300 mg |
| light anhydrous silicic acid | 10 mg |
| Pharmasol B115 | 450 mg. |

(Production Method)
The procedure of Example 1 was repeated.

Comparative Example 3

(Formulation)

| | |
|---|---|
| ketoprofen | 50 mg |
| monodecanoyl-glycerol | 300 mg |
| light anhydrous silicic acid | 10 mg |
| Pharmasol B115 | 450 mg. |

(Production Method)
The procedure of Example 1 was repeated.

Comparative Example 4

The formulation and procedure of Example 8 were repeated but the carboxyvinyl polymer was omitted and the amount of the suppository base (Witepsol W35) was increased to compensate therefor.

Comparative Example 5

The formulation and procedure of Example 8 were repeated but the tetrahydrozoline hydrochloride was omitted and the amount of the suppository base (Witepsol W35) was increased to compensate therefor.

Comparative Example 6

The formulation and procedure of Example 8 were repeated but the tetrahydrozoline hydrochloride and carboxyvinyl polymer were omitted and the amount of the suppository base (Witepsol W35) was increased to compensate therefor.

Comparative Example 7

(Formulation)

| | |
|---|---|
| phenylephrine hydrochloride | 1.3 mg |
| dibucaine | 1.8 mg |
| hydrocortisone acetate | 1.3 mg |
| zinc oxide | 40 mg |
| light anhydrous silicic acid | 20 mg |
| carboxyvinyl polymer | 20 mg |
| Pharmasol B115 | 1570 mg. |

(Production Method)
The procedure of Example 1 was repeated.

Comparative Example 8

(Formulation)

| | |
|---|---|
| phenylephrine hydrochloride | 1.3 mg |
| dibucaine | 1.8 mg |
| hydrocortisone acetate | 1.3 mg |
| zinc oxide | 40 mg |
| light anhydrous silicic acid | 20 mg |
| carboxyvinyl polymer | 20 mg |
| monolauroyl-glycerol | 630 mg |
| Pharmasol B115 | 940 mg. |

(Production Method)
The procedure of Example 1 was repeated.

Comparative Example 9

(Formulation)

| | |
|---|---|
| phenylephrine hydrochloride | 1.3 mg |
| dibucaine | 1.8 mg |
| hydrocortisone acetate | 1.3 mg |
| zinc oxide | 40 mg |
| light anhydrous silicic acid | 20 mg |
| carboxyvinyl polymer | 20 mg |
| monodecanoyl-glycerol | 630 mg |
| Pharmasol B115 | 940 mg. |

(Production Method)

The procedure of Example 1 was repeated.

Test Example 1

Measurement of Melting Point of Suppository (Sample)

As the samples, the suppositories of Examples 1, 2 and 9 were used. Also, the suppositories of Comparative Examples 1 to 3 and 7 to 9 were used as the comparative samples.

(Test Method)

The melting point of each suppository was measured in accordance with the method of Muranishi et al. ["Zazai: Seizai kara Rinsho Oyo made "Suppositories: From Production to Clinical Application)", page 64, 1985, Nanzan-do] with the use of a suppository penetrometer (Model PM3, manufactured by ERWEKA, Germany). A test tube containing a suppository was immersed in water bath at 30° C. for 10 minutes. Next, the temperature was elevated at a rate of 0.2° C./min. The water temperature at which a test needle penetrated through the suppository was referred to as the melting point thereof. The melting point determined by adding 5 ml of water to the test tube was referred to as the melting point under the moist conditions in body cavity, while the one determined without adding water was referred to as the melting point under dry storage conditions. Also, the conditions of the suppositories were monitored at 37° C. corresponding to the body temperature in human body cavity.

(Results)

Table 1 summarizes the data determined under dry and moist conditions and at 37° C.

TABLE 1

|  | Melting point (° C.) | | Conditions at 37 ° C. | |
| --- | --- | --- | --- | --- |
|  | Dry | Moist | Dry | Moist |
| Ex. 1 | 40.0 | 33.6 | solid | liquid |
| Ex. 2 | 45.1 | 36.8 | solid | liquid |
| Ex. 9 | 43.5 | 37.0 | solid | gel |
| Comp. Ex. 1 | 34.4 | 34.5 | liquid | liquid |
| Comp. Ex. 2 | 48.9 | 39.5 | solid | solid |
| Comp. Ex. 3 | 34.1 | 32.0 | liquid | liquid |
| Comp. Ex. 7 | 37.0 | 36.8 | gel | gel |
| Comp. Ex. 8 | 50.3 | 47.2 | solid | solid |
| Comp. Ex. 9 | 36.5 | 34.0 | gel | gel |

At 37° C., the suppositories of Examples 1, 2 and 9 were in a solid state under dry conditions but liquefied or gelled under moist conditions. On the other hand, the suppositories of Comparative Examples 1, 3, 7 and 9 were in a state of liquid or gel both under dry and moist conditions. These comparative samples showed little difference in melting point between dry and moist conditions. Although the suppositories of Comparative Examples 2 and 8 showed differences in melting point between dry and moist conditions, these samples were in a solid state under both conditions.

Test Example 2

Measurement of Drug-releasing Rate (Sample)

The suppository of Example 1 was used as the sample.

(Test Method)

A suppository was placed on a dialysis membrane and the bottom of the membrane was closed with a closer provided with a weight (manufactured by SPECTRUM, USA). Next, it was immersed in a test solution (pH 7.0, 1,000 ml) at 37° C. and the drug thus released into the solution was measured by high performance liquid chromatography.

(Results)

Table 2 shows the ketoprofen-releasing rates after 4 hours. The suppositories of Example 1 showed a high ketoprofen-releasing rate.

TABLE 2

|  | Ex. 1 | C.Ex. 1 | C.Ex. 2 | C.Ex. 3 |
| --- | --- | --- | --- | --- |
| Releasing rate(%) | 90.8 | 95.2 | 52.8 | 89.8 |

Test Example 3

Retention Test in vitro (Sample)

The suppository of Example 8 was used as the sample, while that of Comparative Example 4 was used as the comparative sample.

(Test Method)

To evaluate the retention of the suppository in an affected part conveniently in vitro, a test was performed by applying the method of Sentikar-Fantelli.

A cellulose membrane (dialysis membrane, size 36: Viskase Sales Corporation) having been well washed with deionized water was tied with a string at the bottom and then fixed in a glass tube (2 cm in diameter×20 cm). Then the sample and 5 ml of water were poured thereinto from the top. Immediately thereafter, warm water (37° C.) was circulated under a hydraulic pressure of 15±2 cm $H_2O$. The location of the suppository was examined 10, 30 and 60 minutes thereafter. To judge the migration distance of the suppository, the circulating water was rapidly cooled simultaneously with the termination of the test so as to solidify the suppository. Then the sample was taken out together with the cellulose membrane and thoroughly dried. Subsequently, the suppository was weighed in the section 0 to 8 cm from the tied site.

(Results)

Table 3 shows the weight ratios (%) of the suppositories. The sample of Example 8 showed a retention rate exceeding 90% at every point (10, 30 and 60 minutes), while the sample of Comparative Example 4 showed a retention rate lower than 50% at every point.

TABLE 3

| Time (min) | Ex. 8 | C.Ex. 4 |
| --- | --- | --- |
| 10 | 99.3 | 47.2 |
| 30 | 98.0 | 40.9 |
| 60 | 93.8 | 49.4 |

Test Example 4

Edema Inhibition Test (Sample)

The suppository of Example 8 was used as the sample, while those of Comparative Examples 5 and 6 were used as the comparative samples.

(Test Method)

After fasting for 24 hours, male Wistar rats (weight: 150–170 g) were arbitrarily classified into groups each having 12 animals. A swab immersed in 0.16 ml of an inflammation-inducing solution (6% croton oil in ether:distilled water:pyridine:ether=10:1:4:5:) was inserted into the anus of each animal for 10 seconds to thereby induce inflammation. Immediately thereafter, the sample or the comparative samples (each 3 mm in diameter, 10 mm in length per 100 g body weight) were administered to the rats.

After the administration of the suppositories, the anus of each animal was clipped to prevent the suppositories from leakage. After 6 hours, the rectum was taken out and the tissues 5 to 20 mm apart from the anus were collected. These tissues were weighed in the wet state and the recto-anus coefficient (RAC) was calculated as an indication of edema. Moreover, the edema inhibitory rate was calculated from the RAC thus determined.

(Results)

Compared with the comparative samples, the suppository of Example 8 showed an extremely high edema inhibitory rate, as Table 4 shows.

$$RAC = \frac{\text{wet weight of rectum/anus}}{\text{body weight (g)}} \times 1000.$$

Edema inhibitory ratio (%) =

$$\frac{1 - (RAC \text{ of test group} - RAC \text{ of untreated group})}{RAC \text{ of comparative group} - RAC \text{ of untreated group}} \times 100.$$

TABLE 4

| Group | RAC | Edema inhibitory ratio (%) |
|---|---|---|
| untreated | 0.79 ± 0.03 | — |
| comparative | 2.15 ± 0.07 | — |
| Ex. 8 | 1.19 ± 0.04 | 70.6 |
| C.Ex. 5 | 1.58 ± 0.03 | 41.9 |
| C.Ex. 6 | 1.99 ± 0.04 | 11.8 |

What is claimed is:

1. A composition for suppositories which comprises (A) a fatty base, (B) monodecanoyl-glycerol, (C) monolauroyl-glycerol, (D) a powder insoluble in the fatty base, (E) a drug for suppositories and (F) a retentive base for intracavity administration.

2. The composition for suppositories as claimed in claim 1, wherein the content of a fatty base (A) is from 30 to 85% by weight, the content of monodecanoyl-glycerol (B) is from 0.1 to 30% by weight, the content of monolauroyl-glycerol (C) is from 5 to 65% by weight, the content of a powder insoluble in the fatty base (D) is from 0.1 to 20% by weight, the content of a drug for suppositories (E) is from 0.1 to 20% by weight and the content of a retentive base for intracavity administration (F) is from 0.1 to 20% by weight, each based on the total weight of the composition for suppositories.

3. The composition for suppositories as claimed in claim 1 or 2, wherein said retentive base for intracavity administration is one or more members selected from among acrylic acid polymers, Polygam alkali metal salts, layered silicate minerals and starch acrylate.

4. The composition for suppositories as claimed in claim 3, wherein said acrylic acid polymer is carboxyvinyl polymer.

5. A composition for suppositories prepared by adding a vasoconstrictor to the composition for suppositories as claimed in claim 1 or 2.

6. A composition for suppositories, comprising (A) a fatty base, (B) monodecanoyl-glycerol, (C) monolauroyl-glycerol, (D) a powder insoluble in the fatty base and (E) a drug for suppositories, wherein the content of the fatty base (A) is from 25 to 85% by weight, the content of monodecanoyl-glycerol (B) is from 0.1 to 30% by weight, the content of monolauroyl-glycerol (C) is from 10 to 70% by weight, the content of the powder insoluble in the fatty base (D) is from 0.1 to 20% by weight and the content of the drug for suppositories (E) is from 0.1 to 20% by weight, each based on the total weight of the composition for suppositories.

* * * * *